US00PP10817P

United States Patent [19]

Olsthoorn

[11] Patent Number: Plant 10,817

[45] Date of Patent: Mar. 2, 1999

[54] SPATHIPHYLLUM PLANT NAMED 'SWEET PABLO'

[76] Inventor: Petrus Cornelius Maria Olsthoorn, Zwartendijk 25A, 2681 LN Monster, Netherlands

[21] Appl. No.: 932,198

[22] Filed: Sep. 17, 1997

[51] Int. Cl.[6] ..... A01H 5/00

[52] U.S. Cl. ..... Plt./364

[58] Field of Search ..... Plt./88.1, 364

*Primary Examiner*—Howard J. Locker

*Attorney, Agent, or Firm*—C. A. Whealy

[57] ABSTRACT

A distinct cultivar of Spathiphyllum plant named Sweet Pablo, characterized by its glossy green leaves that are held horizontal to the petiole; freely branching habit which gives a dense and full appearance to the plants; vigorous and rapid growth rate; early flowering; numerous large white flowers that are positioned just above the foliage on strong and erect peduncles; and long-lasting flowers.

4 Drawing Sheets

The present invention relates to a new and distinct cultivar of Spathiphyllum plant, botanically known as Spathiphyllum Schott, and hereinafter referred to by the cultivar name Sweet Pablo.

The new cultivar is a product of a planned and controlled breeding program conducted by the inventor in Monster, The Netherlands. The objective of the breeding program is to create new Spathiphyllum cultivars with good plant form, good leaf and flower proportion, rapid growth rate, and early and continuous flowering.

The new cultivar originated from a cross by the inventor between the proprietary Spathiphyllum Schott selection 91317-3 as the female or seed parent and the proprietary Spathiphyllum Schott selection 92116-11 as the male or pollen parent. The cultivar Sweet Pablo was discovered and selected by the inventor in 1994 as a plant within the progeny of the stated cross in a controlled environment in Monster, The Netherlands. Compared to plants of the female parent, plants of the new Spathiphyllum have lighter green leaves. Compared to plants of the male parent, plants of the new Spathiphyllum are more compact. Additionally plants of the male parent have green spathes whereas plants of the new Spathiphyllum have white spathes.

Asexual propagation of the new cultivar by division and by tissue culture at Naaldwijk, The Netherlands, has shown that the unique features of this new Spathiphyllum plant are stable and reproduced true to type in successive generations of asexual propagation.

The new Spathiphyllum has not been observed under all possible environmental conditions. The phenotype may vary somewhat with variations in environment such as temperature and light intensity, without, however, any variance in genotype.

The following traits have been repeatedly observed and are determined to be the unique characteristics of Sweet Pablo. These characteristics in combination distinguish Sweet Pablo as a new and distinct cultivar:

1. Glossy green leaves that are held horizontal to the petiole.
2. Freely branching habit which gives a dense and full appearance to the plants.
3. Vigorous and rapid growth rate.
4. Early flowering.
5. Numerous large white flowers that are positioned just above the foliage on strong and erect peduncles.
6. Long-lasting flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. The photograph on the first sheet comprises a top perspective view of a typical potted plant of Sweet Pablo.

The photograph on the second sheet comprises a close-up view of the foliage of Sweet Pablo.

The photograph on the third sheet comprises a close-up view of a typical spathe and spadix of Sweet Pablo.

The photograph on the fourth sheet comprises a close-up view of the back of a typical spathe of Sweet Pablo.

DETAILED BOTANICAL DESCRIPTION

In the following description, color references are made to The Royal Horticultural Society Colour Chart except where general terms of ordinary dictionary significance are used. The following observations and measurements describe plants grown in Monster, The Netherlands, in a glass greenhouse under typical commercial conditions with day and night temperatures averaging 21° and 19° C., respectively.

Botanical classification: Spathiphyllum Schott cultivar Sweet Pablo.

Parentage:

*Female parent.*—Proprietary Spathiphyllum Schott selection 91317-3.

*Male parent.*—Proprietary Spathiphyllum Schott selection 92116-11.

Propagation: By division or by tissue culture.

*Time to initiate and develop roots.*—Winter: About 35 days at 23° C. Summer: About 28 days at 23° C.

*Rooting habit.*—Freely branching, numerous fleshy roots.

Plant Description:

*Plant shape.*—Upright, inverted triangle, symmetrical.

*Growth habit.*—Erect when young, becoming outwardly arching as leaves develop. Numerous side shoots give plants a full, dense appearance. Appropriate for 12 to 17-cm containers.

*Plant height.*—About 55 cm from soil level to top of leaf plane.

*Plant vigor.*—High vigor and rapid growth rate.

*Time to flowering.*—Usually 14 to 18 weeks after planting, plants will start flowering. p2 *Time to finishing.*—About 23 weeks are required to produce a finished 14-cm plant with two flowering stems.

*Foliage descriptions.*—Shape: Lanceolate. Aspect: Mature leaves held perpendicular to petiole. Length: About 32.5 cm. Width: About 13 cm. Apex: Apiculate. Base: Cuneate. Margin: Entire. Surface: Rippled. Texture: Glabrous and glossy. Color: Young, top side: 137A/139A. Young, under side: 138B/138C. Mature, top side: 137A/139A. Mature, under side: 138A. Venation, top side: 144A. Venation, under side: 144B. Petiole length: About 30 cm. Petiole color: 137A139A.

*Petiole diameter.*—About 5 mm for largest mature leaves. Geniculum diameter: About 6 mm.

Flower description:

*Flower arrangement.*—Large concave spathe with spadix held above the foliage. Numerous flowers arise from leaf axils. Flowering continuous. Flowers persistent.

*Flower longevity.*—Flowers are long-lasting, generally maintaining white color for about 6 weeks on the plant depending on light and temperature levels.

*Quantity of flowering stems.*—About 15 flowering stems are formed per year.

*Fragrance.*—Sweet, perfume like.

*Spathe.*—Appearance: Somewhat shiny. Angle: Erect, upright. Shape: Lanceolate to elliptic. Apex: Apiculate. Base: Cuneate. Margin: Entire. Length: About 20 cm. Width: About 9 cm. Aspect: Concave, curving over the spadix. Color: When opening: 145A. Open flower: Front: 155D. Back: 155D with prominent green midvein, 143C.

*Spadix.*—Axis: Longitudinal. Cross section: Rounded. Length: About 7 cm. Diameter: About 1.65 cm. Color: 158B.

*Flowers.*—Quantity per spadix: About 150. Shape: Conical. Size: About 2 mm. Stigma shape: Rounded. Pollen color: Mature: 158D. After senescence: 159A.

*Peduncle.*—Aspect: Strong and erect. Length: About 47.5 cm. Color: 137A/139A.

Disease resistance: No known Spathiphyllum diseases observed to date on plants grown under commercial greenhouse conditions.

Seed development: Seed development has not been observed.

It is claimed:

1. A new and distinct cultivar of Spathiphyllum plant named Sweet Pablo, as illustrated and described.

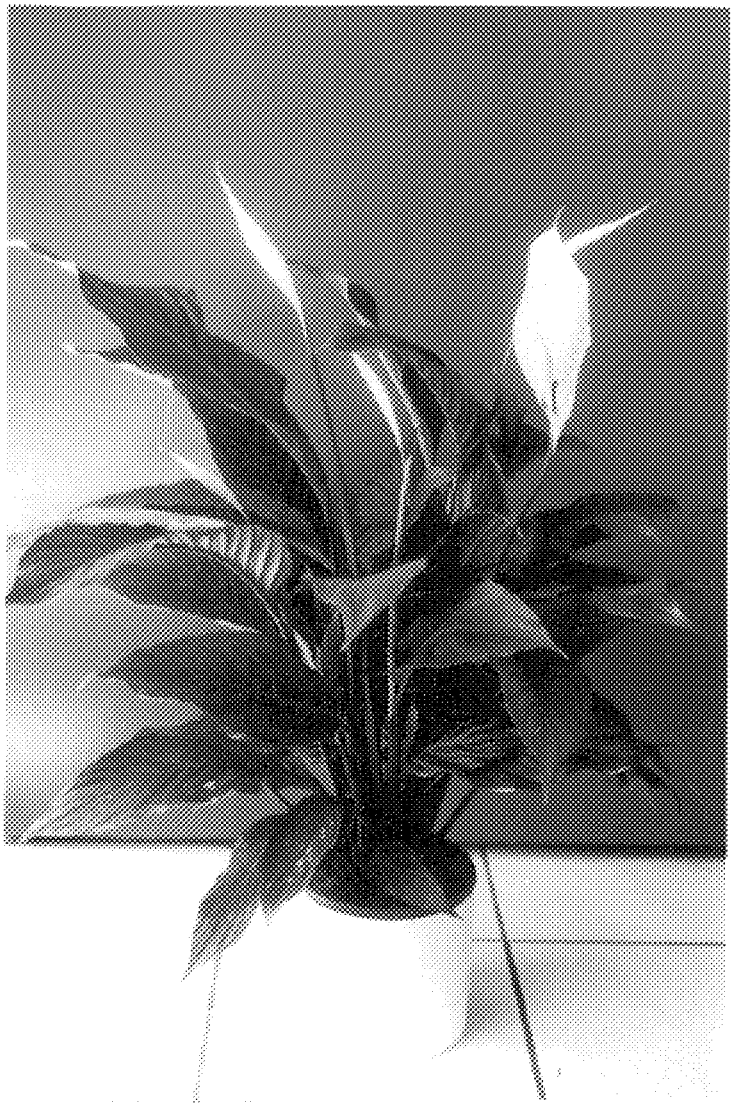

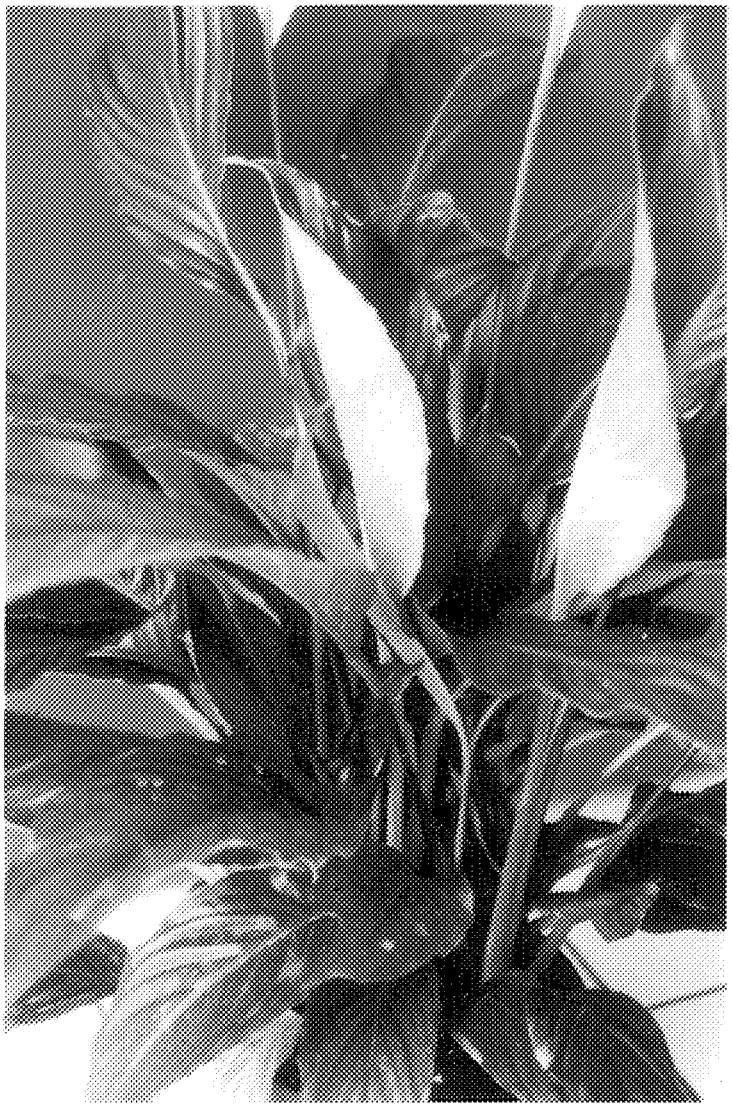

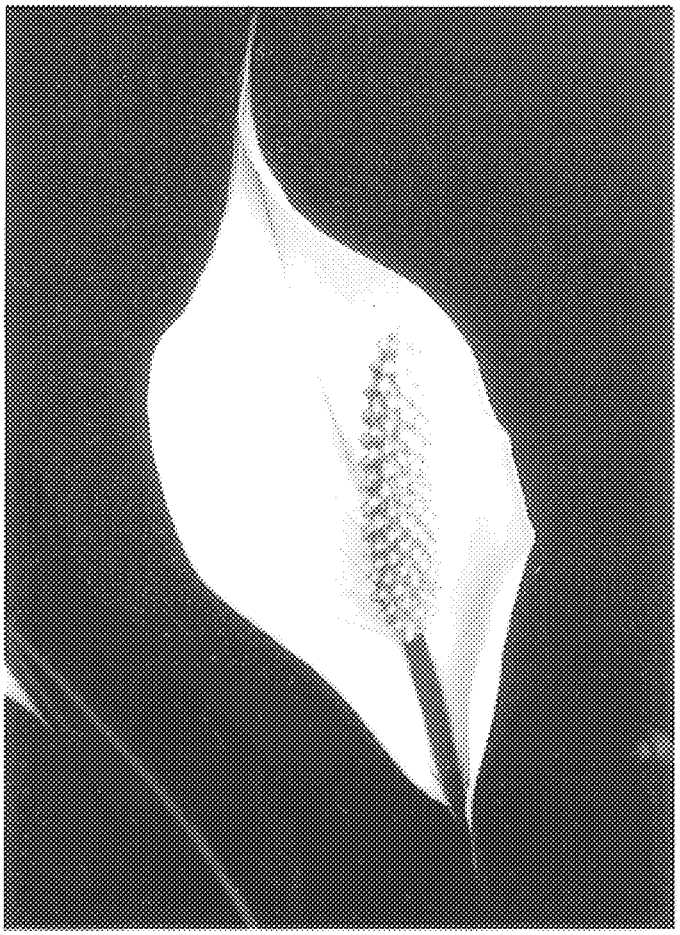

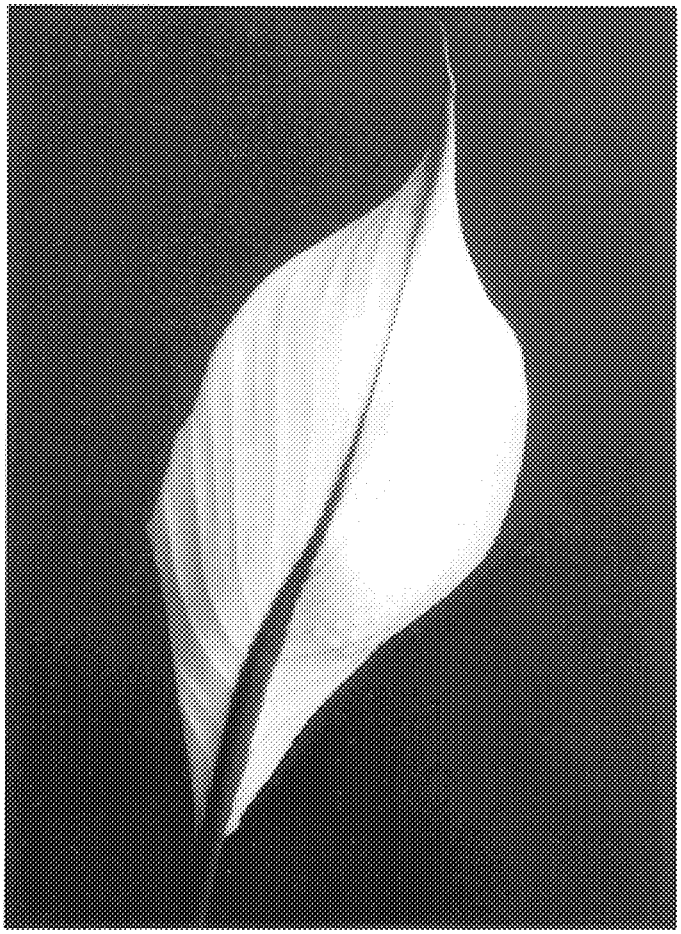

* * * * *